United States Patent
Ernst et al.

(10) Patent No.: US 7,339,085 B2
(45) Date of Patent: Mar. 4, 2008

(54) METHOD FOR PRODUCING 2,7-DIMETHYL-OCTA-2,4,6-TRIENEDIAL

(75) Inventors: Hansgeorg Ernst, Speyer (DE); Klaus Henrich, Haßloch (DE); Andreas Keller, Speyer (DE)

(73) Assignee: BASF Aktiengesellschaft (DE)

( * ) Notice: Subject to any disclaimer, the term of this patent is extended or adjusted under 35 U.S.C. 154(b) by 38 days.

(21) Appl. No.: 10/588,683

(22) PCT Filed: Feb. 4, 2005

(86) PCT No.: PCT/EP2005/001138

§ 371 (c)(1),
(2), (4) Date: Aug. 8, 2006

(87) PCT Pub. No.: WO2005/077874

PCT Pub. Date: Aug. 25, 2005

(65) Prior Publication Data

US 2007/0244344 A1    Oct. 18, 2007

(30) Foreign Application Priority Data

Feb. 10, 2004  (DE) ...................... 10 2004 006 579

(51) Int. Cl.
*C07C 45/45* (2006.01)
(52) U.S. Cl. ...................... 568/486; 568/494
(58) Field of Classification Search ...................... None
See application file for complete search history.

(56) References Cited

U.S. PATENT DOCUMENTS 5,338,888 A * 8/1994 Paust et al. .................. 568/596
5,886,196 A   3/1999 Fürbringer

FOREIGN PATENT DOCUMENTS

CH        321106      4/1957
EP     0 784 042      7/1997

OTHER PUBLICATIONS

Britton, G. et al., Ed., "Carotenoids", vol. 2: Synthesis, (1996) pp. 301-302.
Britton, G. et al., Ed., "Carotenoids", vol. 2: Synthesis, (1996) pp. 117-118.
Makin, S. M. et al., "Chemistry of Unsaturated Ethers, XVIII. Synthesis of Unsaturated Dialdehydes and Their Derivatives", J. Gen. Chem, USSR 34 (1964), pp. 64-68.

* cited by examiner

*Primary Examiner*—Sikarl A. Witherspoon
(74) *Attorney, Agent, or Firm*—Connolly Bove Lodge & Hutz LLP

(57) ABSTRACT

The present invention relates to an improved process for preparing 2,7-dimethylocta-2,4,6-trienedial of the formula I,

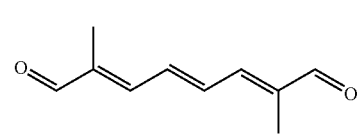

I by
a) double enol ether condensation of a butenedial bisacetal of the formula II with an enol ether of the formula III,

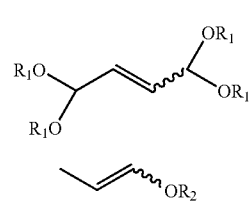

II

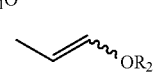

III in the presence of a Lewis acid catalyst to give a condensation product of the formula IV,

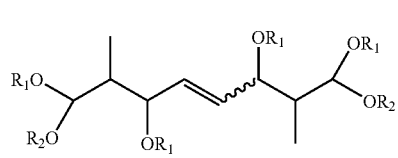

IV where the radicals $R_1$ and $R_2$ in formulae II to IV are independently of one another $C_1$-$C_6$-alkyl;

b) hydrolysis of the acetal groups of IV by adding an aqueous acid to form the dialdehyde of the formula V;

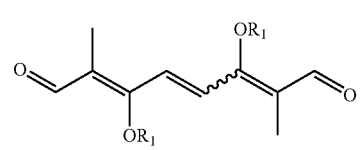

V d) crystallization of I from the reaction mixture,
Wherein process steps a) to d) are carried out in the presence of an inert, water-immiscible organic solvent.

11 Claims, No Drawings

METHOD FOR PRODUCING 2,7-DIMETHYL-OCTA-2,4,6-TRIENEDIAL

RELATED APPLICATIONS

This application is a national stage application (under 35 U.S.C. 371) of PCT/EP2005/001138 filed Feb. 4, 2005, which claims benefit of German application 10 2004 006 0579.9 filed Feb. 10, 2004.

The present invention relates to an improved process for preparing 2,7-dimethylocta-2,4,6-trienedial of the formula I, referred to as $C_{10}$-dial hereinafter.

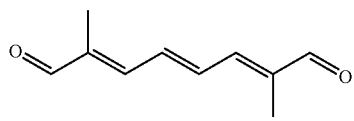

I $C_{10}$-Dial I is required as an important intermediate for technical processes for preparing carotenoids, e.g. lycopene, β-carotene and astaxanthin (see: "Carotenoids", Vol. 2, "Synthesis", page 7 et seq., page 92 et seq., and page 274 et seq.; Birkhäuser Verlag, 1996).

A good way of obtaining I is therefore particularly important for a commercial processs for preparing these pigments, which are in demand.

Various processes for preparing $C_{10}$-dial are known (see: "Carotenoids", Vol. 2, page 117/118), including double enol ether condensation of butenedial bisacetals of the formula II with propenyl ethers of the formula III to give a hexaalkoxy-dimethyloctene intermediate of the formula IV, followed by a double acetal cleavage to give a dialkoxy dial of the formula V and a double alkanol elimination.

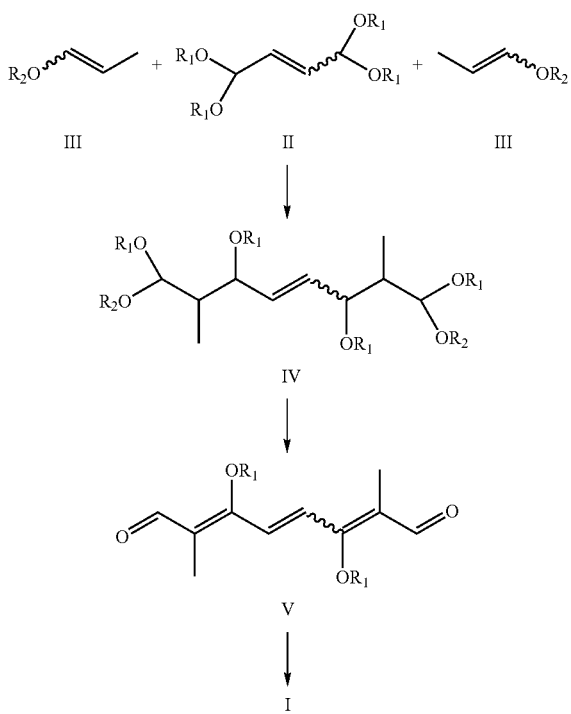

Various conditions are mentioned in the literature for carrying out this synthetic sequence. According to Swiss patent 321106, in a first step butenediol bisacetal II is condensed in the presence of an acidic catalyst with a propenyl ether III, particular emphasis being placed on boron trifluoride etherate, $ZnCl_2$, $TiCl_4$, $AlCl_3$ and $SnCl_4$. This process is carried out in the absence of an additional solvent. In the next step, the acetal groups of the intermediate IV are hydrolyzed in an acidic medium to form the final product I with simultaneous elimination of $R_1OH$ from the 2,3 and 6,7 positions. Addition of a water-miscible solvent such as dioxane, THF or ethylene glycol dimethyl ether in combination with aqueous phosphoric acid is mentioned as particularly advantageous. The stated yield is 56% of theory.

Alternatively, the reaction of IV to give the $C_{10}$-dial I can also be carried out according to Swiss patent 321106 by heating with aqueous acetic acid for several hours. $C_{10}$-dial is subsequently precipitated by dilution with water.

According to J. Gen. Chem. USSR, 34, 64 et seq. (1964), the abovementioned enol ether condensation of the compounds II and III ($R_1=R_2=CH_3$) is carried out in the presence of $ZnCl_2+BF_3$ etherate without addition of a solvent. The hexamethoxy compound IV is isolated by distillation in a yield of 71%. Conversion of IV into the $C_{10}$-dial I is carried out by heating in 6% strength aqueous phosphoric acid for several hours, simultaneously distilling out the methanol formed. A yield of 65% of theory (based on compound IV) is achieved. The overall yield of 46% of theory (based on compound II) is moreover insufficient for a commercial process.

The enol ether condensation (with $R_1=CH_3$; $R_2=C_2H_5$) under very similar conditions is described in "Carotenoids", Vol. 2, "Synthesis", pages 301/302, (Birkhäuser Verlag, 1996). The crude yield of IV after basic workup—without further purification—is stated as being 98% of theory. The hydrolysis and elimination steps are carried out by heating IV in 90% strength aqueous acetic acid with addition of 15% sodium acetate. Addition of water precipitates, in a yield of 70%, a brown product of unsatisfactory purity, so that recrystallization is necessary from toluene with addition of activated carbon. The overall yield of $C_{10}$-dial I is only about 57% of theory (based on compound II).

EP 784042 describes the enol ether condensation (with $R_1=R_2=CH_3$) in the presence of hydrogen bis(oxalato) borate as acidic catalyst in the absence of a solvent. The acetal protective groups are hydrolyzed by heating the reaction mixture undiluted while distilling out the methanol produced. $C_{10}$-dial I precipitates after the reaction mixture is made alkaline with 15% strength sodium hydroxide solution. No statement is made about the purity of the product; a yield of 67% is found after LC analysis.

All the processes described at the outset provide only an unsatisfactory overall yield of $C_{10}$-dial. In addition, the purity of the product precipitated from the aqueous medium is insufficient for it to be employable directly in the synthesis of carotenoids, so that additional recrystallization is frequently necessary.

It was therefore an object of the present invention to provide a process for preparing 2,7-dimethylocta-2,4,6-trienedial in high yield and in high purity.

This object has been achieved by a process for preparing 2,7-dimethylocta-2,4,6-trienedial of the formula I,

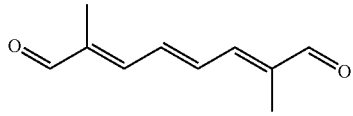

by
a) double enol ether condensation of a butenedial bisacetal of the formula II

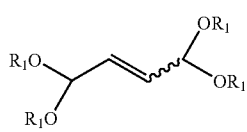

with an enol ether of the formula III,

in the presence of a Lewis acid catalyst to give a condensation product of the formula IV,

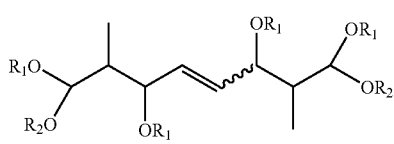

where the radicals $R_1$ and $R_2$ in formulae II to IV are independently of one another $C_1$-$C_6$-alkyl;
b) hydrolysis of the acetal groups of IV by adding an aqueous acid to form the dialdehyde of the formula V;

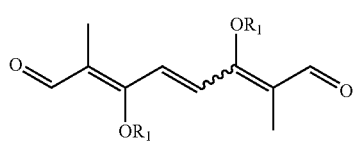

c) conversion of V into the dialdehyde I by reacting with an aqueous base and
d) crystallization of I from the reaction mixture, Wherein process steps a) to d) are carried out in the presence of an inert, water-immiscible organic solvent.

Alkyl radicals $R_1$ and $R^2$ are linear or branched $C_1$-$C_6$-alkyl chains, e.g. methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Preferred alkyl radicals are methyl, ethyl, n-propyl and 1-methylethyl, particularly preferably methyl and ethyl, very particularly preferably methyl.

The spatial arrangement of the substituents on the C—C double bonds in compounds II, III and IV, and the configuration of the central C—C double bond in compound V is irrelevant to the feasibility of the process of the invention. Possibilities in this connection are both isomerically pure cis-trans compounds, and cis-trans mixtures. Ordinarily, cis-trans mixtures of the compounds II to V will be employed in the context of the present invention.

The C—C double bonds in the 2,7-dimethylocta-2,4,6-trienedial of the formula I which is prepared according to the invention are predominantly in the all-trans configuration. The proportion of all-trans $C_{10}$-dial is ordinarily in the range between 85 and 95%.

"Inert water-immiscible organic solvents" mean in particular open-chain or cyclohydrocarbons such as, for instance, hexane, heptane or cyclohexane, aromatic hydrocarbons such as benzene, toluene or xylene, dialkyl ethers such as, for instance, diisopropyl ether, di-n-butyl ether or methyl tert-butyl ether, $C_1$ to $C_6$ alkyl esters of alkanecarboxylic acids such as, for example, ethyl acetate, and mixtures of these solvents. Aromatic hydrocarbons are preferably employed, particularly preferably toluene.

In the first step of the process of the invention, the double enol ether condensation of II with III, the procedure is ordinarily such that compound II is mixed with an acidic catalyst. The concentration of II is not critical; it is ordinarily from 5 to 15% by weight, preferably about 10% by weight, based on the total weight of the solution.

Suitable catalysts are generally the Lewis acids mentioned in the literature for enol ether condensations of this type (see, inter alia, "Carotenoids", Vol. 2, p. 29/30); that have to be mentioned as preferred are $BF_3$ etherate, $ZnCl_2$ and $FeCl_3$, and mixtures thereof. Anhydrous $FeCl_3$ is particularly preferred.

The catalysts are employed in an amount of from 0.05 to 10 mol %, preferably in an amount of from 0.1 to 5 mol % (based on compound II). The reaction temperature in the enol ether condensation is in the range from about 0° C. to 50° C., preferably from 20° C. to 30° C.

The amounts of enol ether III employed are ordinarily in the range from 1.9 to 2.3 mol, preferably in the range from 2 to 2.2 mol, particularly preferably 2.1 mol, per mol of butenedial bisacetal II employed.

The enol ether condensation of the invention is advantageously carried out in such a way that the butenedial bisacetal II is mixed with the Lewis acid, and the enol ether III is metered in continuously over several hours, preferably 3 to 6 h.

One advantage of the process of the invention is that no workup of the reaction mixture from the enol ether condensation is necessary. On the contrary, the subsequent acetal hydrolysis can be carried out in the reaction mixture from the first stage without workup.

Acidic catalysts suitable for stage b) are aqueous solutions of inorganic acids such as, for instance, sulfuric acid, nitric acid, phosphoric acid, boric acid or hydrohalic acids, and acidic salts of polybasic acids such as, for instance, alkali metal or alkaline earth metal bisulfates. Also suitable are aqueous solutions of salts with an acidic pH for the acetal cleavage, such as, for example, aqueous solutions of $FeCl_3$ or $ZnCl_2$, so that it is necessary if appropriate merely to add water to the reaction mixture from the enol ether condensation without further addition of an acid. Besides these inorganic acids, also suitable for this acetal cleavage are aqueous solutions of organic acids such as, for instance, sulfonic acids (methanesulfonic acid, benzenesulfonic acid, toluenesulfonic acid) and other organic acids such as, for instance, citric acid, oxalic acid, formic acid and lower alkanecarboxylic acids such as, for example, acetic acid.

Preferred acidic catalysts are sulfuric acid, nitric acid, phosphoric acid or hydrohalic acids or mixtures thereof, and sulfuric acid is particularly preferably used.

The concentration of the acid in the aqueous solution is in the range from about 0.1 to 20% by weight, preferably about 2 to 10% by weight, and the reaction temperature is in the range from 20° C. to the respective boiling point of the solvent employed, preferably in the range from 30° C. to 90° C., particularly preferably in the range from 70° C. to 90° C.

The acetal cleavage can take place in one stage, in which case the alcohol formed is removed from the acetal cleavage/acetalization equilibrium preferably by distillation under atmospheric pressure or reduced pressure. Alternatively, the resulting alcohol can also be removed by extraction into the aqueous phase. In this case, if appropriate, a 2 to 3-stage procedure is advantageous to complete the conversion.

The acetal cleavage (conversion of compound IV into compound V) is followed by the elimination reaction c) to give the $C_{10}$-dial. This is done by adding a base to the solution of the dialkoxy dial V. The acidic aqueous phase of the acetal cleavage can in this case be made alkaline directly, but in the preferred embodiment of the process of the invention it is removed before addition of base.

Bases suitable for the elimination reaction are aqueous solutions of alkali metal and alkaline earth metal hydroxides, carbonates and bicarbonates, trialkylamines such as, for instance, triethylamine or alkali metal or alkaline earth metal salts of organic acids such as, for instance, acetates, formates or oxalates. Aqueous solutions of sodium hydroxide, sodium carbonate or sodium bicarbonate or mixtures thereof are preferred, and an aqueous solution of sodium bicarbonate is particularly preferred.

The concentration of the base in the aqueous solution is about 0.2 to 15% by weight, preferably about 1 to 10% by weight. The reaction temperature is in the range from 20° C. to the respective boiling point of the solvent employed, preferably in the range from 30° C. to 90° C., particularly preferably in the range from 70° C. to 90° C. The resulting alcohol can if desired be distilled out under atmospheric pressure or reduced pressure.

After completion of the elimination reaction, the aqueous phase is separated off. The organic phase can if desired be washed with water to remove water-soluble impurities.

The product precipitated from the organic phase can be isolated by filtration in a manner known per se. Required product still dissolved in the mother liquor can be obtained by further concentration and renewed crystallization, but particularly advantageously by recycling the mother liquor with partial discharge (discharge rate about 5 to 15%, preferably 10%).

$C_{10}$-Dial I is obtained in this way in a yield of at least 80% of theory (based on compound II) and with a purity of more than 99.5% (according to GC). This product is suitable without a further purification step for the final carotenoids stages mentioned at the outset.

In another embodiment of the process of the invention, the base can be added undiluted to the solution of V in the respective inert organic solvent. Bases suitable in this case are, beside trialkylamines such as, for example, triethylamine, tripropylamine or tributylamine, also alkali metal or alkaline earth metal hydroxides, carbonates and bicarbonates, and salts of organic acids such as, for example, acetates, formates or oxalates. These bases can be employed in catalytic amount, but preferably in molar amount (based on compound V) or in a multiple molar excess. After completion of the elimination, the basic elimination catalyst is washed out by one or more water washings.

The process of the invention is to be described in more detail by means of the following examples.

EXAMPLE 1

179.1 g (1.013 mol) of butenedial bisacetal II ($R_1$=methyl) and 0.35 g (2.16 mmol) of anhydrous iron(III) chloride were introduced into 2 l of toluene. 147.6 g (2.026 mol) of 1-methoxypropene III ($R_2$=$CH_3$) were fed in over the course of 4 h. During this, the reaction temperature was kept at 25° C. After the end of feeding in, the mixture was stirred at +25° C. for 2 h. Then 400 g of 2% strength aqueous sulfuric acid were added, and the mixture was heated to 80° C. and stirred at this temperature for 4 h. The aqueous phase was then separated off. Once again 400 ml of 2% strength sulfuric acid were added and, after stirring at 80° C. for 2 h, the aqueous phase was separated off. This operation was repeated once again. Then 1000 g of a 5% strength sodium bicarbonate solution were added, and the mixture was stirred at a temperature of 80 to 85° C. for 3 h. The lower aqueous phase was separated off, and the upper organic phase washed at 80° C. with 500 ml of water at 80° C. The aqueous phase was separated off, and the organic phase was concentrated to 1 l under reduced pressure. The concentrated organic phase was cooled to 0° C., and the resulting suspension of I was stirred at 0° C. for 1 h. The product was filtered off, washed twice with 250 ml of cold toluene each time and dried in a vacuum drying oven at 50° C./20 mbar.

| Final weight: | 128.3 g of $C_{10}$-dial I |
|---|---|
| Yield: | 77.3% of theory |
| M.p.: | 162° C.-163° C. |
| Purity (GC): | 100% |

A further 10.5 g (6.3% of theory) could be isolated by concentrating the combined mother liquor and washings.

It was also possible to isolate required product still present in mother liquor and washings due to residual solubility by recycling to the crystallization of the next batch (see example 2).

EXAMPLE 2

98.9 g (0.55 mol) of butenedial II ($R_1$=methyl) and 0.268 g (1.65 mmol) of anhydrous iron (III) chloride were introduced into 682 g of toluene. 79.3 g (1.10 mol) of 1-methoxypropene III ($R_2$=$CH_3$) were fed in over the course of 4 h. During this, the reaction temperature was kept at 25° C. After the end of feeding in, the mixture was stirred at 25° C. for 2 h.

855 g of reaction product mixture were obtained.

A 389 g portion (which corresponded to a proportion of 0.455 of the complete reaction) was mixed with 125 ml of 0.5% strength sulfuric acid. The mixture was stirred at 85°

C. for 5 h, during which the methanol produced was distilled out under atmospheric pressure.

Then, without previous removal of the sulfuric acid-containing aqueous phase, 110 g of a 5% strength sodium bicarbonate solution were fed into this two-phase mixture at 85° C. over the course of 1 h, and the mixture was stirred at 85° C. for a further 3 h, during which the methanol produced was continuously distilled out under atmospheric pressure. The lower aqueous phase was then separated off at 80° C. The upper phase at 80° C. washed with 75 ml of water at 80° C.

The aqueous phase was separated off.

The organic phase was concentrated under 400 mbar. This entailed simultaneous feeding in of 90% of the mother liquor and the whole of the washings from an identical previous batch. When the final volume was about 250 ml, it was cooled to 0° C. The resulting suspension of I was stirred at 0° C. for 1 h. The product was filtered off, washed twice with 50 ml of cold toluene each time and dried in a drying oven at 50° C./20 mbar.

| Final weight: | 34.46 g of $C_{10}$-dial I |
| --- | --- |
| Yield: | 84.1% of theory |
| M.p.: | 163° C.-164° C. |
| Purity (GC): | 100% |

Mother liquor and washings were collected separately. 90% of the mother liquor and the whole of the washings were recycled to the concentration step for an identical following batch. 10% of the mother liquor were discharged and disposed of.

EXAMPLE 3

A solution of 80.1 g of enol ether condensation product IV ($R_1$=$R_2$=$CH_3$) in 500 ml of toluene which was prepared in analogy to example 1 was mixed with 250 ml of 2.5% strength aqueous phosphoric acid. The mixture was heated to an internal temperature of 85 to 90° C. and methanol was distilled out over a period of 5 h. The lower aqueous phase was separated off. The upper organic phase was analyzed by gas chromatography. It comprised 86.6% dimethoxy dial V, 4.5% enol ether condensation product IV and 7.2% $C_{10}$-dial I.

EXAMPLE 4

A solution of 8.01 g of enol ether condensation product IV ($R_1$=$R_2$=$CH_3$) in 50 ml of toluene which was prepared in analogy to example 1 was stirred with 25 ml of 10% strength aqueous oxalic acid solution at 80° C. for 1 h. The organic phase was then analyzed by gas chromatography:

89.3% dimethoxy dial V, 1.7% enol ether condensation product IV.

EXAMPLE 5

50.6 mg (0.5 mmol) of triethylamine were added to a solution of 2.28 g (10 mmol) of dimethoxy dial V in 20 ml of toluene which was prepared in analogy to example 1. The mixture was then heated under reflux for 8 h. The GC analysis thereafter showed 98.5% $C_{10}$-dial I and 1.5% dimethoxy dial V.

EXAMPLE 6

2.86 g (34 mmol) of solid sodium bicarbonate were added to a solution of 2.86 g (12.5 mmol) of dimethoxy dial V in 25 ml of toluene which was prepared in analogy to example 1. The suspension was heated under reflux for 8 h. The GC analysis thereafter showed 92% $C_{10}$-dial I and 7.5% dimethoxy dial V.

We claim:

1. A process for preparing 2,7-dimethylocta-2,4,6-trienedial of the formula I,

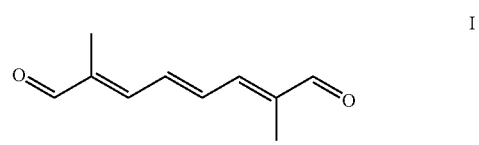

by
a) double enol ether condensation of a butenedial bisacetal of the formula II

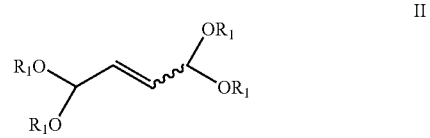

with an enol ether of the formula III,

in the presence of a Lewis acid catalyst to give a condensation product of the formula IV,

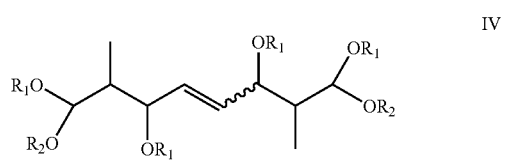

where the radicals $R_1$ and $R_2$ in formulae II to IV are independently of one another $C_1$-$C_6$-alkyl;
b) hydrolysis of the acetal groups of IV by adding an aqueous acid to form the dialdehyde of the formula V;

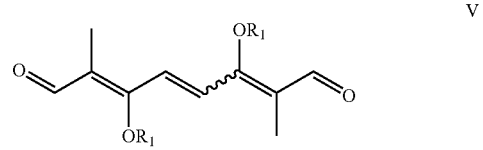

c) conversion of V into the dialdehyde I by reacting with an aqueous base and
d) crystallization of I from the reaction mixture, wherein process steps a) to d) are carried out in the presence of an inert, water-immiscible organic solvent.

2. The process according to claim 1, wherein toluene is used as solvent in all of process steps a) to d).

3. The process according to claim 1, wherein the double enol ether condensation in process step a) is carried out in the presence of $ZnCl_2$, $BF_3$ etherate or $FeCl_3$ or of mixtures thereof.

4. The process according to claim 3, wherein anhydrous $FeCl_3$ is employed as Lewis acid catalyst.

5. The process according to claim 1, wherein aqueous sulfuric, nitric, phosphoric or hydrohalic acid or mixtures thereof are employed for the acetal cleavage in process step b).

6. The process according to claim 5, wherein aqueous sulfuric acid is used.

7. The process according to claim 1, wherein aqueous solutions of alkali metal or alkaline earth metal hydroxides, carbonates or bicarbonates are employed for the elimination reaction in process step c).

8. The process according to claim 7, wherein an aqueous sodium bicarbonate solution is used.

9. The process according to claim 1, wherein the radicals $R_1$ and $R_2$ independently are methyl, ethyl, n-propyl or 1methylethyl.

10. The process according to claim 1, wherein the radicals $R_1$ and $R_2$ independently are methyl or ethyl.

11. The process according to claim 1, wherein the radicals $R_1$ and $R_2$ are methyl.

* * * * *